United States Patent [19]

Bussey

[11] 4,294,245

[45] Oct. 13, 1981

[54] PERIOPERATIVE APPLICATION OF ELECTRONIC PAIN CONTROL IN COMBINATION WITH ANESTHETIC AGENTS

[75] Inventor: Joseph G. Bussey, Austell, Ga.

[73] Assignee: Stimtech, Inc., Minneapolis, Minn.

[21] Appl. No.: 133,211

[22] Filed: Mar. 24, 1980

[51] Int. Cl.³ .............................................. A61N 1/30
[52] U.S. Cl. .............................. 128/207.21; 128/421
[58] Field of Search ................. 128/1 R, 1 C, 207.21, 128/419, 421, 422, 303.1, 329 A

[56] References Cited

U.S. PATENT DOCUMENTS

| | | | |
|---|---|---|---|
| 3,682,162 | 8/1972 | Colyer | 128/207.21 |
| 3,911,930 | 10/1975 | Hagfors et al. | 128/421 |
| 3,991,755 | 11/1976 | Vernon et al. | 128/207.21 |
| 4,141,359 | 2/1979 | Jacobsen et al. | 128/419 R |
| 4,237,896 | 12/1979 | Lines | 128/419 R |

FOREIGN PATENT DOCUMENTS

| | | | |
|---|---|---|---|
| 2449 | of 1859 | United Kingdom | 128/207.21 |
| 972926 | 10/1964 | United Kingdom | 128/1 C |
| 243789 | 9/1969 | U.S.S.R. | 128/1 C |

*Primary Examiner*—William E. Kamm
*Attorney, Agent, or Firm*—Audley A. Ciamporcero, Jr.

[57] ABSTRACT

The patient is prepared for surgery in conventional fashion, but further including the administration of sterile transcutaneous electrodes proximal to the enervation loci of the prospective incision. Electrical stimulation is commenced, an anesthetic agent is administered, and the electrical stimulation is readjusted to the highest levels attainable short of tetany. The surgery proceeds with substantially reduced maintenance quantities of anesthetic.

7 Claims, No Drawings

PERIOPERATIVE APPLICATION OF ELECTRONIC PAIN CONTROL IN COMBINATION WITH ANESTHETIC AGENTS

FIELD OF THE INVENTION

This invention relates to alleviation of patient sensation during surgery, in particular through the vehicle of combined application of anesthetic agents and transcutaneous nerve stimulation.

BACKGROUND OF THE INVENTION AND PRIOR ART

At one time the crucial phase of surgical illness was thought to be the anesthesia itself, with the chance of survival depending in large measure upon the patient's response to anesthetic agent. More modern thought holds that while the parameters of anesthesia during the operation are of high importance, pre-anesthesia and to perhaps a greater extent post-anesthetic care plays a great part in determining whether the outcome will be satisfactory. It is an object of the present invention to provide techniques which facilitate the perioperative anesthesia and analgesia treatment continuum. Modern practice dictates choice of an anesthetic agent and procedure based upon several relevant risk considerations, including the age, prior anesthetic experience and emotional condition of the patient, habits and skill of the surgeon, the patient's physical position required for the procedure, and the need to avoid agents or techniques which can unjustifiably be implicated if a complication were to arise. Indeed, the asthenic, the elderly and the chronically ill will generally require minimal anesthesia virtually irrespective of the other conditions. Even the robust, however, who generally will tolerate high levels of anesthetic concentration, often will benefit from relatively minimal though adequate concentrations of anesthetic.

It is a further object of the present invention to provide techniques which allow minimum administration of anesthetic agents. The evolution of anesthetic practice has progressed to ever more complex physiological mechanisms, and a huge variety of agents, administrative techniques, and brands. For example, originally the anesthesia choice lay among ether, nitrous oxide, or chloroform, straightforwardly administered with simple devices. More recently, with proliferation of highly specialized agents, it has become standard practice to give combinations of agents in a balanced technique, each agent for a specific purpose —regional anesthesia for analgesia and muscle relaxation, an appropriate agent administered intravenously for loss of consciousness, and for a suitable inhalant for maintenance of unconsciousness. Not surprisingly, proliferation of anesthetic agents, and administration of a combination of agents in balanced technique, each agent for a specific purpose, increases the risk of untoward reactions by the patient. Indeed, some studies have indicated that 13% of patients admitted to a medical ward suffer some kind of unusual drug reaction, and many are admitted to the hospital for that reason alone. The average out-patient was found to take about six different drugs habitually, while the very ill hospitalized patient may be given as many as twenty. Thus, the possibiltiy for interaction among drugs is considerable, and anesthetics are no exception. Further, straightforward reactions may be genetic in origin, such as perhaps may be true of malignant hyperpyrexia during anesthesia. It is an object of the present invention to minimize untoward reactions occasioned by plural anesthesia agents, or with other drugs or agents. Another problem presented to the anesthetist in particular but also to the surgical team, in general, is presented by the habitual user of drugs or alcohol, who may have vastly altered tolerance to drugs in general and anesthetics in particular.

It is a summary object of the present invention to provide techniques whereby the anesthesiologist, attending physicians, and the surgical team may properly and adequately conduct a surgical procedure, alleviate patient discomfort or sensation, and maintain the patient after surgery, while minimizing risks, trauma, untoward drug interaction and associated occasional adverse effects of anesthesia.

SUMAMRY OF THE INVENTION

In accordance with the principles of the present invention, the hazards attendant to administration of anesthetic agents are vastly reduced by procedures which permit considerable decrease in the amount of anesthetic agents administered. In particular, the principles of the present invention are based on joint administration of transcutaneous electrical nerve stimulation and anesthetic agents, with a high degree of local pain alleviation being accomplished through the transcutaneous stimulation, and the balance of desired anesthetic effects being taken up by the anesthetic agents.

In accordance with principles of the present invention, the area of prospective incision is prepared, and sterile transcutaneous electrodes are adhered to the patient proximal to the enervation loci of the prospective incision. Electrical stimulation is commenced, at maximum levels which the patient tolerates comfortably. Thereupon, anesthetic agents are applied, which as desired may include inhaled gaseous agents, intravenous agents, or muscle relaxants. When the desired effects and procedures are completed (e.g. intubation, loss of consciousness, specified level of general anesthesia, or the like), the intensity of electrical stimulation is increased to the higher of the maximum available stimulation amplitude, or just short of the point of involuntary muscle contraction (tetany). Upon such maximization of the effect of stimulation, the balance of the required alleviation of sensation is achieved by maintenance of anesthetic agent administration, but typically at levels vastly lower than those which would be required if the transcutaneous stimulation were not employed.

BEST MODE OF CARRYING OUT THE INVENTION

The concept of transcutaneous electrical nerve stimulation is rapidly becoming an accepted procedure for post-operative applications, as well as for alleviation of chronic pain, such as of the lower back. For example, U.S. Pat. No. 3,911,930 entitled METHOD AND STRUCTURE OF PREVENTING AND TREATING ILEUS, AND REDUCING ACUTE PAIN BY ELECTRICAL PULSE STIMULATION, of Hagfors, et al, which is assigned to the assignee hereof, describes and claims the utilization of transcutaneous electrical nerve stimulation for pain control. Other patents and applications of the assignee hereof and others relate to various improvements in the field of transcutaneous stimulation, including improvements to the electronics and signal processing aspects thereof, and to the composition and configuration of electrodes which are capable of administering the stimulating signals to the subject. The former class of improvements, dealing with signal processing improvements and electronics, include provision for scanning, (i.e., continuous variation, through prescribed ranges, of pulse height, pulse width, and pulse frequency for optimization of efficacy), alternating of pulse polarity, shaping of individual pulses themselves, and provision of bursts of short duration pulses, separated by time periods of different character. Improvements in the latter class, relating to the electrodes themselves, make provision for conductive adhesive gels of synthetic natural composition, layered composite structures for strength and desired current density characteristics, and a variety of coupling techniques which enhance operation but which foster economical re-use of certain more expensive portions and disposability of economically less significant portions of the system.

In accordance with the principles of the present invention, it is anticipated that transcutaneous electrical nerve stimulation may be achieved in accordance with the ever developing state of the art, in terms of electronics, power sources, electrode structure and materials, and signal processing techniques. That is, it is anticipated that to the extent that improvements occur generally in the field of transcutaneous stimulation, they will likewise be applicable and advantageous in accordance with the principles of the present invention, whereby they are applied conjunctively with anesthetic agents.

It is to be noted that it is undesirable for the transcutaneous nerve stimulation in accordance with the principles of the present invention to provide spurious interference with associated monitoring or surgical equipment being utilized in the operating theater, and to the extent that such interference takes place, is evident that provision should be made to eliminate the untoward effects of the interference. For example, it has been found that spurious interaction of transcutaneous nerve stimulation equipment with electroencephalograph or electrocardiograph equipment equipment may be minimized by coordinating their operation with the stimulating unit, and utilizing conventional sample and hold processing techniques for the monitoring equipment. Similar approaches have in the past been employed in the operating room with respect to other sources of interference (e.g., electrocautery instruments) which are known to generate spurious interference signals. Those skilled in the art have developed numerous shielding and signal processing techniques which unobtrusively and without hazard allow for joint operation of the interference source, and the interfered with monitoring equipment. It is anticipated that the incorporation of transcutaneous nerve stimulation equipment into surgery suites will occasion the same sorts of solutions if and when the interference problems occur.

In accordance with the principles of the present invention, preparation for surgery is to include the application of sterile transcutaneous electrodes proximal to the enervation loci of the prospective incision. That is, it is desired that the electrodes generally overlay the nerve systems which serve the site of the incision. In a preferred approach, the electrodes of the sort also used conventionally for post-operative pain control, and are applied in a fashion whereby they can continue to be used for pain control after the surgery has been completed. A superior product which is available for this purpose is the electrode which is currently available from Stimtech, Inc. of Minneapolis, Minnesota under the trade designation "S-20 POST OPERATIVE ELECTRODE". Such electrodes demonstrate excellent uniformity of charge distribution in the range of 1500 Nano Coulombs per square centimeter to 5 Nano Coulombs per square centimeter, which is a preferred charge density range for application in accordance with the principles of the present invention.

Also for purposes of application of the principles of the present invention, a variety of nerve stimulating equipment is suitable, with preferred operation being from 3 to 150 pulses per second in frequency, from 20 to 400 microseconds in pulse duration (although the range of 250 to 400 microseconds in practice seldom is used), and an amplitude range which may well be up to 60 milliamperes (although this parameter largely will be dependent upon the musculature and nervous structure of the patient, and in fact some individuals may tolerate much higher amplitude levels without the onset of tetany). It is further contemplated that the state of the art signal processing may be utilized, such as combinations of bursts with or without alternating polarity; frequency, amplitude, and duty cycle scanning, and the like. The aforementioned Stimtech, Inc. of Minneapolis, Minnesota, among others, has several nerve stimulater models commerically available which meet the aforementioned desired parameter ranges.

It is to be noted that the state of the anesthesia administration art is one which, although quite sophisticated, nevertheless is largely empirical. Thus, in terms of general, all embracing rules, it is difficult if not impossible to derive rules whereby particular agents, or combinations of agents, are to be applied for a given procedure, or for a patient with given personal and demographic characteristics. Correspondingly, it is equally difficult to render such formulations in accordance with the principles of the present invention. Nevertheless, as the following examples show, it is believed generally true that application of the principles of the present invention provide opportunity for substantial reduction of anesthetic agents to be administered in combination with transcutaneous nerve stimulation, as opposed to that which would be required in the absence of such stimulation. Indeed, in many instances, the anesthetic agent was administered in sufficiently low dosages that the condition of the patient was more akin to "amnesia" than to "general anesthesia" as such. For purposes of the instant disclosure, the term "general anesthesia" is utilized, intending to embrace any such depth of anesthesia as may be required, together with transcutaneous stimulation, in order to render the patient insensate to the procedure being followed, including but not limited to such instances where patient unconsciousness is desired. In the following examples, brand name anesthetics are utilized, but without intention of limitation to such brands.

EXAMPLE I

Placebo: 41 year old female having exploratory laparotomy, salpingo-oophretcomy, extraperitonealization of the right ureter and incidental appendectomy. This patient required 500 mg. of intravenous Sodium Pentothal, 34 cc. of intravenous Sublimase and in addition, a continuous IV infusion of Anectine to maintain muscular relaxation.

Example 1A: 27 year old female having cystoscopy and retrograde studies done prior to the initiation of intraoperative transcutaneous neuro stimulation. During that phase of the procedure, which lasted for one and a half hours, the patient required 375 mg. of Pentothal and 2% Ethrane and in addition, 2 cc. of intravenous Sublimase and an Anectine infusion for muscular relaxation.

In the second portion of the procedure, which included exploratory laparotomy and cholecystectomy, transcutaneous nerve stimulation was utilized on a continuous basis. No Sodium Pentothal or Sublimase were required, and the concentration of Ethrane was decreased to 0.5%. Through such second portion, no increase in the reactivity of the patient was perceived.

Example 1B: 34 year old female having exploratory laparotomy and cholecystectomy. Stimulation with intraoperative transcutaneous electrical nerve stimulation was initiated immediately following induction of anesthesia. Total operative anesthesia requirements were induction with 600 mg. of Penthothal administered prior to stimulation and intubation. Total operative requirement of 5 cc. of Sublimase, the first 2 cc. being given during anesthetic induction and prior to stimulation. A slow infusion of Anectine with total dose 300 mg. was given during the operative procedure to maintain muscle relaxation.

Example 1C: 37 year old female undergoing exploratory laparotomy, vagotomy and pyloroplasty following perforation of an acute duodenal ulcer. Transcutaneous stimulation was begun immediately following induction of anesthesia. During intubation, 375 mg. of Sodium Pentothal and 2 cc. IV Sublimase was administered. Following the initiation of intraoperative transcutaneous nerve stimulation, 190 mg. of Pentothal and 2 cc. of intravenous Sublimase was administered. A slow infusion of Anectine, total dose 400 mg. was given during the 2 hours and 10 minutes of surgery to maintain muscle relaxation.

This anesthetic technique included the initiation of transcutaneous electrical nerve stimulation with electrodes placed near the mid-axillary line bilaterally and at the levels of the 4th and 12th thoracic nerves. General anesthesia was induced with the Pentothal and the Anectine was administered to allow endotracheal intubation. After this, anesthesia was maintained at a minimal level using intravenous Sublimase and a mixture of Nitrous Oxide and oxygen. Although the anesthesia was kept at a level allowing frequent spontaneous movement of the arms and legs, there was satisfactory relaxation of the abdominal musculature without the necessity to continue intravenous Anectine during the procedure. Following the procedure, anesthesia was terminated as the skin was closed and the patient was sufficiently reactive to move voluntarily to the stretcher from the operating table. It was the estimate of the anesthesiologist in attendance that three to four times the amount of anesthetic agents actually applied would normally be utilized for such procedure and that the additional requirement of continuous muscular paralysis would have been essential for exploration and closure of the abdomen.

EXAMPLE II Placebo: 74 year old male having exploratory laporotomy, lysis of adhesions, take-down of stenotic Bilroth II anastomosis with conversion to a Roux-Y gastrojejunostomy. Despite efforts to maintain a very light anesthesia due to the patient's age and generally poor medical status, anesthetic requirements were a total of 750 mg. of Sodium Pentothal and 13 cc. of intravenous Sublimase as well as 8 mg. of intravenous Pavulon for muscle relaxation. In spite of the amounts of medications given, the anesthetic level was suboptimal and relaxation poor.

Example 2A: 76 year old Caucasian male having cholecystectomy, exploratory laparotomy, duodenotomy, sphincterotomy and sphincteroplasty with removal of obstructing common duct stone. Anesthesia induction was performed following administration of 10 mg. of IV Valium, 2 cc. of IV Sublimase and 4 mg. of IV Pavulon. Trans-cutaneous stimulation was initiated immediately following induction. Subsequently, total anesthesia administered during 2 hours and 40 minutes surgery included 10 mg. of IV Valium, 2 mg. of IV Pavulon and 375 mg. of Sodium Pentothal. Although some movement of the extremeties was noted during the operative procedure, abdominal relaxation was satisfactory throughout.

EXAMPLE III

Placebo: 25 year old male having repair of left inguinal hernia, recurrent. Anesthetic requirements during the 1 hour and 15 minute operative procedure included 625 mg. of Pentothal, 6 cc. of IV Sublimase, and a slow Anectine drip with 100 mg. total dose.

Example 3A: 56 year old male having repair of left inguinal hernia; during the entire 1 hour and 15 minute procedure, transcutaneous nerve stimulation was applied. Total anesthetic required was 200 mg. Sodium Pentothal and 4 cc. of IV Sublimase, with relaxation satisfactory without any additional muscle relaxants.

Example 3B: 21 year old female having repair of umbilical hernia. During the entire 1 hour operative time, transcutaneous electrical nerve stimulation was applied. Total anesthetic requirements were 375 g. Pentothal and 2 cc. Sublimase. Muscle relaxants were discontinued following induction of the anesthesia, with no further relaxants necessary for satisfactory relaxation.

Example 3 C: 37 year old male having bilaterial inguinal herniorrhaphy and vasectomy, with a 1 hour and 55 minute operative time. Anesthesia was induced using 350 mg. IV Sodium Pentothal and 100 mg. IV Anectine with 2½% Ethrane.

Following induction, transcutaneous electrical nerve stimulation was initiated. Subsequent to utilization of the stimulation, Anectine was not necessary for satisfactory relaxation. Pentothal, total dosage after induction, was merely 75 mg., and Ethrane concentration was reduced to one-half of one percent, and subsequently to one-quarter of one percent. Although the patient moved his extremities somewhat during the procedure, muscle relaxation in the operative area was satisfactory during the time of stimulation.

The foregoing examples demonstrate vastly reduced requirements for anesthetics, due to utilization of transcutaneous nerve stimulation in combination therewith. It is to be understood that the foregoing sets forth preferred and illustrative embodiments of the principles of the present invention, but that numerous alternations will occur to those of ordinary skill in the art.

What is claimed is:

1. An improved method of preparing a patient for surgery, and for alleviating sensation of a patient during surgery, wherein the improvement comprises applying transcutaneous electrical nerve stimulation at least one point proximal to the site of incision, administering an anesthetic agent, and proceeding with surgery with the patient under the combined synergistic influence of said simulator and said agent.

2. A method as described in claim 1 wherein applying step comprises applying the maximum stimulation intensity tolerated by the patient free of tetany, and wherein said agent is administered at concentrations substantially below those required without simultaneous application of said stimulation agent.

3. A method as described in claim 1 wherein said applying step comprises applying a continuous pulse stimulating signal having a pulse frequency in the range of 20 to 400 microseconds, at a charge density of 1550 to 5 nanocoulombs per square centimeter.

4. A method as described in claim 1 wherein said applying step comprises applying intermittent bursts of stimulating pulses.

5. A method as described in claim 1 wherein said applying step comprises applying a pulse stimulating signal having successive pulses of respective alternating polarity about a datum level.

6. A method of avoiding patient sensation at a surgical site during surgery comprising:
    (a) preparing the area of prospective incision.
    (b) adhering sterile transcutaneous electrodes proximal to enervation loci of the prospective incision;
    (c) commencing electrical simulation of the patient via said electrodes;
    (d) administering at least one anesthetic agent to the patient at concentrations needed to produce a state of general anesthesia; and
    (e) proceeding with incision and surgery with patient sensation alleviated by the combined effect of said stimulation and said agent.

7. A method as described in claim 6 wherein said commencing step comprises stimulating the patient at the highest levels of intensity which the patient can tolerate comfortably, and wherein said method further comprises, after said administering step, the step of readjusting the intensity of said stimulation upwardly to the lower of maximum intensity available or to the maximum level tolerated by the patient short of tetany.

* * * * *